United States Patent
Kopkalli et al.

(10) Patent No.: US 10,029,964 B2
(45) Date of Patent: Jul. 24, 2018

(54) AZEOTROPIC OR AZEOTROPE-LIKE COMPOSITIONS OF 3,3,3-TRIFLUOROPROPYNE AND WATER

(71) Applicant: Honeywell International Inc., Morris Plains, NJ (US)

(72) Inventors: Haluk Kopkalli, Staten Island, NY (US); Hang T. Pham, Amherst, NY (US); Daniel C. Merkel, West Seneca, NY (US)

(73) Assignee: Honeywell International Inc., Morris Plains, NJ (US)

( * ) Notice: Subject to any disclaimer, the term of this patent is extended or adjusted under 35 U.S.C. 154(b) by 226 days.

(21) Appl. No.: 15/251,468

(22) Filed: Aug. 30, 2016

(65) Prior Publication Data
US 2018/0057434 A1    Mar. 1, 2018

(51) Int. Cl.
*C07C 21/22* (2006.01)
*B01D 3/36* (2006.01)
*C07C 17/383* (2006.01)

(52) U.S. Cl.
CPC ............... *C07C 21/22* (2013.01); *B01D 3/36* (2013.01); *C07C 17/383* (2013.01)

(58) Field of Classification Search
CPC .............................. C07C 21/22; C07C 17/383
See application file for complete search history.

(56) References Cited

U.S. PATENT DOCUMENTS

| | | | |
|---|---|---|---|
| 5,763,706 A | 6/1998 | Tung et al. | |
| 6,013,846 A | 1/2000 | Wismer et al. | |
| 6,365,566 B1 | 4/2002 | Bogdan et al. | |
| 6,475,971 B2 | 11/2002 | Pham et al. | |
| 6,638,987 B2 | 10/2003 | Bogdan et al. | |
| 6,689,924 B1 | 2/2004 | Thenappan et al. | |
| 6,844,475 B1 | 1/2005 | Tung et al. | |
| 7,964,759 B2 | 6/2011 | Ishihara et al. | |
| 8,008,243 B2 | 8/2011 | Tung et al. | |
| 8,114,308 B2 | 2/2012 | Merkel et al. | |
| 8,426,659 B2 | 4/2013 | Holtcamp et al. | |
| 8,519,200 B1 | 8/2013 | Merkel et al. | |
| 8,546,624 B2 | 10/2013 | Pham et al. | |
| 8,747,691 B2 | 6/2014 | Hulse et al. | |
| 8,791,309 B2 | 7/2014 | Zhai et al. | |
| 8,951,431 B2 | 2/2015 | Hulse et al. | |
| 9,000,240 B2 | 4/2015 | Cottrell et al. | |
| 9,045,386 B2 | 6/2015 | Tung et al. | |
| 9,222,177 B2 | 12/2015 | Merkel et al. | |
| 9,272,969 B2 | 3/2016 | Merkel et al. | |
| 2009/0234165 A1 | 9/2009 | Chiu et al. | |
| 2009/0278075 A1 | 11/2009 | Mahler et al. | |
| 2011/0240902 A1 | 10/2011 | Merkel et al. | |
| 2012/0172636 A1 | 7/2012 | Pokrovski et al. | |
| 2013/0092869 A1 | 4/2013 | Boussand | |
| 2013/0221273 A1 | 8/2013 | Merkel et al. | |
| 2014/0264154 A1 | 9/2014 | Merkel et al. | |
| 2014/0284517 A1 | 9/2014 | Hulse et al. | |
| 2016/0355453 A1 | 12/2016 | Ohkubo et al. | |

FOREIGN PATENT DOCUMENTS

| | | |
|---|---|---|
| WO | 9707052 A1 | 2/1997 |
| WO | 2011139945 A2 | 11/2011 |
| WO | 2013161692 A1 | 10/2013 |
| WO | 2015092211 A1 | 6/2015 |
| WO | 2016009946 A1 | 1/2016 |

OTHER PUBLICATIONS

International Search Report and Written Opinion issued in PCT/US2017/046762, dated Nov. 30, 2017, 14 pages.
International Search Report and Written Opinion issued in PCT/US2017/046946, dated Oct. 31, 2017, 13 pages.

*Primary Examiner* — John R Hardee
(74) *Attorney, Agent, or Firm* — Faegre Baker Daniels LLP

(57) ABSTRACT

Azeotropic or azeotrope-like compositions of 3,3,3-trifluoropropyne and water, such as from about 1 to about 50 wt. % water and from about 50 to about 99 wt. % 3,3,3-trifluoropropyne, based on the combined weight of the water and 3,3,3-trifluoropropyne, and methods of producing essentially water free 3,3,3-trifluoropropyne.

20 Claims, No Drawings

AZEOTROPIC OR AZEOTROPE-LIKE COMPOSITIONS OF 3,3,3-TRIFLUOROPROPYNE AND WATER

FIELD OF THE INVENTION

The present invention pertains to azeotropic or azeotrope-like compositions of 3,3,3-trifluoropropyne and water.

BACKGROUND OF THE INVENTION

Traditionally, chlorofluorocarbons (CFCs) like trichlorofluoromethane and dichlorodifluoromethane have been used as refrigerants, blowing agents and diluents for gaseous sterilization. In recent years, there has been universal concern that completely halogenated chlorofluorocarbons might be detrimental to the Earth's ozone layer. Therefore, stratospherically safer alternatives to these materials are desirable.

Consequently, there is a worldwide effort to use fluorine-substituted hydrocarbons which contain fewer or no chlorine substituents. The production of HFCs, i.e., compounds containing only carbon, hydrogen and fluorine, has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFCs by reacting hydrogen fluoride with various hydrochlorocarbon compounds. Such HFCs are not only considered to be much more environmentally advantageous than hydrochlorofluorocarbons (HCFCs) or chlorofluorocarbons (CFCs) because they are not non-ozone depleting, but also they are non-flammable, and non-toxic as compared to the chlorine containing compounds. While HFCs are considered to be much more environmentally advantageous than HCFCs or CFCs because they are non-ozone depleting, recent data indicates that they may also contribute to greenhouse global warming. Accordingly, alternatives to HFCs, HCFCs, and CFCs are also being explored.

Hydrofluoroolefins ("HFOs") have been proposed as possible replacements. It is generally known that HFOs are best used as a single component fluid or azeotropic mixture, neither of which fractionate on boiling and evaporation. The identification of such compositions is difficult due, at least in part, to the relative unpredictability of azeotrope formation. Therefore, industry is continually seeking new HFO-based mixtures that are acceptable and environmentally safer substitutes for CFCs, HCFCs, and HFCs.

3,3,3-trifluoropropyne, also known as "TFPY", is a suitable starting material for various hydrofluoroolefins (HFOs) including but not limited to HFO-1234yf, HFO-1234ze, HCFO-1233zd(Z), and HFO-1225ye, and is also produced as a side product in the production of various hydrofluoroolefins including but not limited to HFO-1234ze, HFO-1234yf, HFCO-1233zd, all of which are well known in the art, and several are described in U.S. Patent Application Publication No. 2009/0234165, assigned to the assignee of the present invention, the disclosure of which is incorporated herein by reference.

Methods to produce 3,3,3-trifluoropropyne are also known in the art, for example, from U.S. Pat. Nos. 7,964,759 and 8,791,309.

New compositions of, methods of separating and purifying, and uses of, 3,3,3-trifluoropropyne are desired.

SUMMARY OF THE INVENTION

The present invention provides azeotropic or azeotrope-like compositions of 3,3,3-trifluoropropyne and water.

In another embodiment, the composition may consist of water and 3,3,3-trifluoropropyne.

In further embodiments, the composition may comprise from about 1 to about 50 wt. % water and from about 50 to about 99 wt. % 3,3,3-trifluoropropyne, based on the combined weight of the water and 3,3,3-trifluoropropyne. Alternatively, the composition may comprise from about 0.1 to about 50 wt. % water and from about 50 to about 99.9 wt. % 3,3,3-trifluoropropyne, based on the combined weight of the water and 3,3,3-trifluoropropyne. The composition may have a boiling point of about $-47°$ C.$\pm 0.5°$ C. at a pressure of about 14.4 psia$\pm 2$ psia. Alternatively, the composition may have a boiling point of about $-46.8°$ C. at a pressure of about 14.4 psia.

In another form thereof, the present invention provides an azeotropic or azeotrope-like composition consisting essentially of from about 1 to about 50 wt. % water and from about 50 to about 99 wt. % 3,3,3-trifluoropropyne, based on the combined weight of the water and 3,3,3-trifluoropropyne, which composition has a boiling point of about $-47°$ C.$\pm 0.5°$ C. at a pressure of about 14.4 psia$\pm 2$ psia. The composition may consist of water and 3,3,3-trifluoropropyne.

In a further form thereof, the present invention provides a method of forming an azeotropic or azeotrope-like composition including the steps of forming a blend consisting essentially of from about 1 to about 50 wt. % water and from about 50 to about 99 wt. % 3,3,3-trifluoropropyne, based on the combined weight of the water and 3,3,3-trifluoropropyne. The composition may consist of water and 3,3,3-trifluoropropyne.

In the foregoing method, the forming step may include forming a blend consisting essentially of from about 0.1 to about 50 wt. % water from about 50 to about 99.9 wt. % 3,3,3-trifluoropropyne, based on the combined weight of the water and 3,3,3-trifluoropropyne, and the composition may have a boiling point of about $-47°$ C.$\pm 0.5°$ C. at a pressure of about 14.4 psia$\pm 2$ psia or alternatively, the composition may have a boiling point of about $-46.8°$ C. at a pressure of about 14.4 psia.

In a further form thereof, the present invention provides a method for producing essentially water free 3,3,3-trifluoropropyne, including the steps of: forming an azeotropic or azeotrope-like composition consisting essentially of from about 1 to about 50 wt. % water and from about 50 to about 99 wt. % 3,3,3-trifluoropropyne, based on the combined weight of the water and 3,3,3-trifluoropropyne, the composition including a water-rich phase and a 3,3,3-trifluoropropyne rich phase; separating the water-rich phase and the 3,3,3-trifluoropropyne rich phase; and removing water from the 3,3,3-trifluoropropyne rich phase to produce 3,3,3-trifluoropropyne having less than 1.0 wt. % water.

In the foregoing method, the forming step may include forming an azeotropic or azeotrope-like composition consisting essentially of from about 0.1 to about 50 wt. % water and from about 50 to about 99.9 wt. % 3,3,3-trifluoropropyne, based on the combined weight of the water and 3,3,3-trifluoropropyne, the composition including a water-rich phase and a 3,3,3-trifluoropropyne rich phase. Also, in the foregoing method, the removing step may further include removing water from the 3,3,3-trifluoropropyne rich phase using at least one removal agent selected from the group consisting of a molecular sieve, calcium sulfate, silica, alumina, and combinations thereof. Alternatively, the removing step may further include separating the water-rich phase and the 3,3,3-trifluoropropyne rich phase by liquid-liquid phase separation. The removing step may also further include removing water from the 3,3,3-trifluoropropyne rich phase to produce 3,3,3-trifluoropropyne having less than 0.5 wt. % water or less than 0.1 wt. % water. Still further, the removing step may further include separating the water-rich phase and the 3,3,3-trifluoropropyne rich phase by distillation.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION

It has been found that 3,3,3-trifluoropropyne (TFPY) forms azeotropic and azeotrope-like compositions or mixtures with water, and more particularly, forms heterogeneous azeotropic and azeotrope-like compositions or mixtures with water.

3,3,3-trifluoropropyne ($CHCCF_3$ or $C_3HF_3$) has a boiling point of about −46° C. at 760 mm Hg and has the following chemical structure:

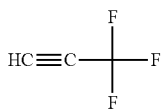

The present invention provides azeotropic or azeotrope-like compositions including or comprising water and 3,3,3-trifluoropropyne and, in other embodiments, the composition may consist essentially of water and 3,3,3-trifluoropropyne and, in still further embodiments, the composition may consist of water and 3,3,3-trifluoropropyne.

The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. Also, as used herein, the term "azeotrope-like" refers to compositions that are strictly azeotropic and/or that generally behave like azeotropic mixtures.

An azeotrope or an azeotrope-like composition is an admixture of two or more different components which, when in liquid form under a given pressure, will boil at a substantially constant temperature, which temperature may be higher or lower than the boiling temperatures of the individual components and which will provide a vapor composition essentially identical to the liquid composition undergoing boiling.

For the purpose of this invention, azeotropic compositions are defined to include azeotrope-like compositions, which is a composition that behaves like an azeotrope, i.e., has constant boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of 3,3,3-trifluoropropyne and water to form an azeotropic or azeotrope-like composition. As used herein, the term "effective amount" is an amount of each component which, when combined with the other component, results in the formation of an azeotrope or azeotrope-like mixture.

The inventive compositions preferably are binary azeotropes which consist essentially of combinations of 3,3,3-trifluoropropyne and water, or consist of combinations of 3,3,3-trifluoropropyne and water. As used herein, the term "consisting essentially of", with respect to the components of an azeotrope-like composition or mixture, means the composition contains the indicated components in an azeotrope-like ratio, and may contain additional components provided that the additional components do not form new azeotrope-like systems. For example, azeotrope-like mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary azeotrope).

As used herein, the terms "heteroazeotrope" and "heterogeneous azeotrope" mean an azeotrope-like composition comprising a vapor phase existing concurrently with two liquid phases.

The invention also provides a method of forming an azeotropic or azeotrope-like composition which comprises forming a blend comprising, consisting essentially of, or consisting of, from about 1 to about 50 weight percent water and about 50 to 99 weight percent 3,3,3-trifluoropropyne, based on the combined weight of the water and 3,3,3-trifluoropropyne, to thereby form an azeotropic or azeotrope-like composition.

The azeotropic or azeotrope-like compositions of the present invention can be produced by combining effective amounts of water with 3,3,3-trifluoropropyne. Any of a wide variety of methods known in the art for combining two or more components to form a composition can be adapted for use in the present methods. For example, water and 3,3,3-trifluoropropyne can be mixed, blended, or otherwise combined by hand and/or by machine, as part of a batch or continuous reaction and/or process, or via combinations of two or more such steps.

In another embodiment, the composition comprises, consists essentially of, or consists of, from about 0.1 to about 50 weight percent water and about 50 to 99.9 weight percent 3,3,3-trifluoropropyne, based on the combined weight of the water and 3,3,3-trifluoropropyne.

The azeotropic or azeotrope-like composition has a boiling point of about −47° C.±0.5° C. at a pressure of about 14.4±2 psia and, in another embodiment, has a boiling point of about −47° C. at a pressure of about 14.4 psia and, in a further embodiment, has a boiling point of about −46.8° C. at a pressure of about 14.4 psia.

The present disclosure also encompasses generating an azeotropic or azeotrope-like composition of 3,3,3-trifluoropropyne and water followed by isolating the azeotrope from impurities. The present disclosure also includes steps for separating and purifying 3,3,3-trifluoropropyne from the azeotropic mixture, as discussed in greater detail below.

3,3,3-trifluoropropyne may be produced using one or more methods that are known in the art, in which 3,3,3-trifluoropropyne is produced as a component of a reactant mixture containing one or more impurities such as 1233zd (E) ((E)-1-chloro-3,3,3-trifluoropropene), 1233zd(Z) ((Z)-1-chloro-3,3,3-trifluoropropene), 1234ze (1,3,3,3-tetrafluoropropene), 1234yf (2,3,3,3-tetrafluoropropene), and 1233xf (2-chloro-3,3,3-trifluoropropene).

The first step in removing 3,3,3-trifluoropropyne from this mixture, or any other mixture containing 3,3,3-trifluoropropyne and an impurity, is by adding water in an effective amount, as defined herein, to form an azeotropic composition of the 3,3,3-trifluoropropyne and water, wherein the impurity itself does not form an azeotropic mixture with 3,3,3-trifluoropropyne, water or a mixture of 3,3,3-trifluoropropyne and water. Thereafter, the azeotropic composition is separated from the impurity using standard separation techniques, such as, but not limited to, liquid-liquid phase separation, distillation, scrubbing, or other art recognized separating means.

The purified azeotrope meets the need in the art for mixtures that have no ozone depletion potential and are negligible contributors to greenhouse global warming and are nonflammable. Such a mixture may be utilized in a wide range of uses such as, but not limited to, refrigerants, blowing agents, propellants and diluents for gaseous sterilization. The azeotrope may be provided in combination with other useful additives or ingredients for such purposes.

Post-purification, it also may be desirable to separate the component parts of the 3,3,3-trifluoropropyne and water azeotrope to a purified form of 3,3,3-trifluoropropyne which is essentially water-free. As used herein, "essentially water-free" or "water-free" refers to compositions of 3,3,3-trifluoropropyne which include less than 1.0 wt. % water, less than 0.5 wt. % water, or less than 0.1 wt. % water.

Separation methods may include any method generally known in the art. In one embodiment, for example, the excess water can be removed from the 3,3,3-trifluoropropyne by liquid-liquid phase separation, though other alternatives include distillation or scrubbing. The remaining water can then be removed from the 3,3,3-trifluoropropyne by distillation and/or the use of one or more drying media or desiccants such as molecular sieves, calcium sulfate, silica, alumina, and combinations thereof.

Purified 3,3,3-trifluoropropyne may be used as an end product such as a refrigerant, blowing agent, propellant, or diluent for gaseous sterilization, or it may be used as a monomer, as an intermediate, or otherwise further processed for the production of alternative HFOs or similar compounds.

The following non-limiting Examples serve to illustrate the invention.

Example 1

A glass vacuum insulated vessel fitted with a dry ice cooled condenser was initially charged with 3,3,3-trifluoropropyne. Water was then added incrementally and the temperature of the mixture was recorded. The temperature of the mixture reached a minimum value and then flattened indicating the formation of a heterogeneous azeotrope. The ambient pressure during the measurements was 14.4 psia.

The measured temperatures are shown in Tables 1 and 2. In Table 2, a physical observation is observed of two separate phases, indicating a heterogeneous azeotrope.

TABLE 1

Ebulliometer measurements of 3,3,3-trifluoropropyne and water at 14.4 psia.
Ebulliometer study of 3,3,3-trifluoropropyne/Water at P = 14.4 Psia

| T (C.) | Wt. % 3,3,3-trifluoropropyne | Wt. % Water |
| --- | --- | --- |
| −46.803 | 100.00 | 0.00 |
| −46.806 | 99.64 | 0.36 |
| −46.809 | 98.93 | 1.07 |
| −46.809 | 97.55 | 2.45 |
| −46.809 | 94.89 | 5.11 |
| −46.810 | 89.98 | 10.02 |
| −46.808 | 85.56 | 14.44 |

3,3,3-trifluoropropyne forms minimum heterogeneous azeotrope with water at P = 14.4 Psia.

TABLE 2

Ebulliometer study of 3,3,3,-trifluoropropyne and water

| Wt. % 3,3,3-trifluoropropyne | Wt. % Water | T (C.) | |
| --- | --- | --- | --- |
| 100.00 | 0.00 | −46.803 | <---AZ |
| 99.64 | 0.36 | −46.806 | composition |
| 98.93 | 1.07 | −46.809 | 2-Phases (ice |
| 97.55 | 2.45 | −46.809 | forming) |
| 94.89 | 5.11 | −46.809 | |
| 89.98 | 10.02 | −46.810 | |
| 85.56 | 14.44 | −46.808 | |

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

The invention claimed is:

1. An azeotropic or azeotrope-like composition consisting essentially of 3,3,3-trifluoropropyne and water.

2. The composition of claim 1, wherein the composition consists of water and 3,3,3-trifluoropropyne.

3. The composition of claim 1, wherein the composition comprises from about 1 to about 50 wt. % water and from about 50 to about 99 wt. % 3,3,3-trifluoropropyne, based on the combined weight of the water and 3,3,3-trifluoropropyne.

4. The composition of claim 3, wherein the composition comprises from about 0.1 to about 50 wt. % water and from about 50 to about 99.9 wt. % 3,3,3-trifluoropropyne, based on the combined weight of the water and 3,3,3-trifluoropropyne.

5. The composition of claim 1, wherein the composition has a boiling point of about −47° C.±0.5° C. at a pressure of about 14.4 psia±2 psia.

6. The composition of claim 5, wherein the composition has a boiling point of about −46.8° C. at a pressure of about 14.4 psia.

7. An azeotropic or azeotrope-like composition consisting essentially of from about 1 to about 50 wt. % water and from about 50 to about 99 wt. % 3,3,3-trifluoropropyne, based on the combined weight of the water and 3,3,3-trifluoropropyne, which composition has a boiling point of about −47° C.±0.5° C. at a pressure of about 14.4 psia±2 psia.

8. The composition of claim 7, wherein the composition consists of water and 3,3,3-trifluoropropyne.

9. A method of forming an azeotropic or azeotrope-like composition comprising forming a blend consisting essentially of from about 1 to about 50 wt. % water and from about 50 to about 99 wt. % 3,3,3-trifluoropropyne, based on the combined weight of the water and 3,3,3-trifluoropropyne.

10. The method of claim 9, wherein the composition consists of water and 3,3,3-trifluoropropyne.

11. The method of claim 9, wherein said forming step comprises forming a blend consisting essentially of from about 0.1 to about 50 wt. % water from about 50 to about 99.9 wt. % 3,3,3-trifluoropropyne, based on the combined weight of the water and 3,3,3-trifluoropropyne.

12. The method of claim 9, wherein the composition has a boiling point of about −47° C.±0.5° C. at a pressure of about 14.4 psia±2 psia.

13. The method of claim 9, wherein the composition has a boiling point of about −46.8° C. at a pressure of about 14.4 psia.

14. A method for producing essentially water free 3,3,3-trifluoropropyne, comprising the steps of:
    forming an azeotropic or azeotrope-like composition consisting essentially of from about 1 to about 50 wt. % water and from about 50 to about 99 wt. % 3,3,3-trifluoropropyne, based on the combined weight of the water and 3,3,3-trifluoropropyne, the composition including a water-rich phase and a 3,3,3-trifluoropropyne rich phase;
    separating the water-rich phase and the 3,3,3-trifluoropropyne rich phase; and
    removing water from the 3,3,3-trifluoropropyne rich phase to produce 3,3,3-trifluoropropyne having less than 1.0 wt. % water.

15. The method of claim 14, wherein said forming step comprises forming an azeotropic or azeotrope-like composition consisting essentially of from about 0.1 to about 50 wt. % water and from about 50 to about 99.9 wt. % 3,3,3-trifluoropropyne, based on the combined weight of the water and 3,3,3-trifluoropropyne, the composition including a water-rich phase and a 3,3,3-trifluoropropyne rich phase.

16. The method of claim 14, wherein said removing step further comprises removing water from the 3,3,3-trifluoropropyne rich phase using at least one removal agent selected from the group consisting of a molecular sieve, calcium sulfate, silica, alumina, and combinations thereof.

17. The method of claim 14, wherein said removing step further comprises separating the water-rich phase and the 3,3,3-trifluoropropyne rich phase by liquid-liquid phase separation.

18. The method of claim 14, wherein said removing step further comprises removing water from the 3,3,3-trifluoropropyne rich phase to produce 3,3,3-trifluoropropyne having less than 0.5 wt. % water.

19. The method of claim 14, wherein said removing step further comprises removing water from the 3,3,3-trifluoropropyne rich phase to produce 3,3,3-trifluoropropyne having less than 0.1 wt. % water.

20. The method of claim 14, wherein said removing step further comprises separating the water-rich phase and the 3,3,3-trifluoropropyne rich phase by distillation.

* * * * *